United States Patent [19]

Bowman et al.

[11] 4,291,692
[45] Sep. 29, 1981

[54] CLOSED-LOOP INFUSION SYSTEM, BOTH METHOD AND APPARATUS, BASED ON REAL TIME URINE MEASUREMENT

[75] Inventors: Robert J. Bowman; Dwayne R. Westenskow, both of Salt Lake City, Utah

[73] Assignee: University of Utah, Salt Lake City, Utah

[21] Appl. No.: 83,027

[22] Filed: Oct. 9, 1979

[51] Int. Cl.³ .............................................. A61M 5/00
[52] U.S. Cl. .............................. 128/214 E; 128/214 F
[58] Field of Search ....... 128/214 E, 214 F, DIG. 12, 128/DIG. 13, 635, 760, 768, 771

[56] References Cited

U.S. PATENT DOCUMENTS

| | | | |
|---|---|---|---|
| 3,732,079 | 5/1973 | Davis | 128/771 |
| 3,754,220 | 8/1973 | Sztamler et al. | 128/771 |
| 3,872,863 | 3/1975 | Lasker et al. | 128/214 E |
| 4,114,144 | 9/1978 | Hyman | 128/214 E |
| 4,173,224 | 11/1979 | Mort et al. | 128/214 E |
| 4,180,771 | 12/1979 | Gockel | 128/635 |

*Primary Examiner*—William E. Kamm
*Attorney, Agent, or Firm*—Thorpe, North, Western & Gold

[57] ABSTRACT

A closed loop system for controlled infusion of fluids, medication or diagnostic substances into a patient based on real time measurement of urine output. Proper urine flow techniques and a self compensating drop count apparatus provide accurate representation as to cumulative number of drops and flow rate, with drop volume variations being compensated by a control algorithm which corrects computer parameters reflecting drop volume to correspond with urine volume measured. This real time urine flow rate is compared with a preset, desired flow rate to develop an error signal which is processed by a computer. Such processing includes modification by a PID control algorithm which governs infusion of fluids into the patient to effect the proper fluid resuscitation, medication or diagnostic treatment.

22 Claims, 2 Drawing Figures

CLOSED-LOOP INFUSION SYSTEM, BOTH METHOD AND APPARATUS, BASED ON REAL TIME URINE MEASUREMENT

BACKGROUND OF THE INVENTION

1. Field of Invention

This invention pertains to closed-loop regulation of infusion of fluids, medications and diagnostic substances. More particularly, it pertains to such infusion regulation by continuous measurement of urine production and composition as an indication of the physiological condition of a patient.

2. Prior Art

The medical profession has long been familiar with the value of urinalysis as an index of the physiological state of a patient, particularly with regard to hematology, metabolism, renal function and the body waste systems. Typically, urinalysis is conducted by obtaining a urine sample and processing it through a series of laboratory tests which are primarily directed to identifying the nature of urine constituents as opposed to urine volume. Although this system has proved adequate for periodic urinalysis, numerous medical conditions require a more constant evaluation of urine output, including production rates and variation.

One such field of primary significance includes medical treatments for burns and major trauma. In addition to monitoring urine constituents, the management of fluid resuscitation is of critical importance. In the past, substantial empirical judgment has been necessary in structuring clinical programs to maintain a patient at proper fluid volumes where substantial portions of his body has been burned or subjected to other major trauma. Obviously, fluid loss in such circumstances is serious and must be remedied and regulated to insure proper recovery.

Historically, a major cause of death from burns was the tremendous fluid shifts that occur immediately post-burn. Many studies have confirmed the importance of sodium-containing crystalloids in volumes up to 15-20% of total body weight as the imperative resuscitation regime following thermal injury. Authors of such studies have emphasized the maintenance of urine output of approximately 30-50 cc/hr. as the most reliable parameter in assessing the adequacy of fluid therapy. Similar studies have led to parallel emphasis on vigorous fluid resuscitation in all forms of major trauma and shock. Although sophisticated invasive techniques have been developed to monitor hemodynamic status and cellular metabolism in such shock, trauma and burn patients, maintenance of adequate urine output remains an important parameter in medical treatment.

This significant role of urine output is based on numerous considerations. For example, the kidney is one of the three vital organs that must be protected by intravascular volume repletion. Also, the maintenance of urine flow at a brisk level tends to protect against the development of acute tubular necrosis and assist in wash-out of myoglobin and hemoglobin from renal tubules. Each of these treatment aspects is especially important to the burn and trauma patient. Furthermore, urine output is a valuable indicator of adequate fluid balance within the patient. Although urine output may correlate rather poorly with fluid administration during inappropriate diuresis and nonoliguric renal failure, the maintenance of urine output above 30 millimeters per hour is strongly suggestive that at least one part of the body is being profused appropriately.

To the physician equipped to monitor cardiac output, mixed venous oxygen tension, etc., urine flow provides confirming evidence of the organism's response to physiologic manipulations and is especially important in vasopressor therapy. This supplemental input from urine flow is even more significant in burn patients since cardiac output is universally depressed with burns and other forms of trauma. Moreover, the cardiovascular response to many types of trauma is still poorly understood. Therefore, in such circumstances, urine output provides a familiar reassurance of the meaning of these more complex parameters. In addition to these technical considerations in support of the importance of urine output as a medical parameter, it is important to note that in a patient having a catheter in place, urine output is an accessible parameter for measurement which does not involve additional invasive procedures which risk infection and add to patient discomfort.

Despite the accessibility and clinical utility for measurement of urine output, however, the medical industry still places primary reliance on manual volumetric measurements of urine flow to control and regulate fluid resuscitation. Some treatment methods still rely on burn fluid formulas which provide a calculated fluid infusion rate based on body weight, extent of burned area, etc. Although such formulas may be useful in developing an initial infusion rate, the broad disparity between actual patient response from the norm, along with the practical limitation of having to manually adjust fluid infusion rates impairs proper manual fluid administration. For example, nurses with many other important duties find it difficult to record frequent urine output, attend to catheter and collection systems, adjust IV's, etc. Too often, the result is confusion as to patient response to fluids, inaccurate recording of outputs and a tendency to over-resuscitate the trauma or burn patient. Because of these practical limitations, little progress has been made in understanding the physiologic balance between fluid therapy and urine output. Although sophisticated bench work has broadened an understanding of kidney function at the cellular level, the translation of such information into treatment methods for the critically ill patient leaves much to be desired.

Initial in-roads into measurement of urine output have been accomplished by the University of Alabama, University of Washington, and Roche, Inc. using instruments which periodically weigh the excreted urine. Other investigators have used ultrasonic measuring devices and volumetric devices; however, such systems tend to be very bulky and to pose contamination and handling problems.

Some progress in computer controlled infusion systems has been realized by the University of Washington and University of Alabama. The Washington system uses a small microprocessor to monitor mean arterial pressure, central venous pressure and hourly urine output. The IV infusion rate is claimed to be automatically controlled to maintain blood pressure and urine output within acceptable limits. Unfortunately, this system requires vascular invasion for arterial and venous monitoring. In addition, the maintenance of consistent blood pressure as a goal of fluid infusion may prove difficult to adapt to a clinical application. This is because the blood pressure of an awake, traumatized man is subject to a myriad of regulating forces including vascular volume, peripheral resistance, catecholamine and other hormonal flux, plus the major contributions of anxiety, pain and level of consciousness. It is questionable, therefore, whether any fluid regime can successfully maintain blood pressure within a narrow range for such patients.

The University of Alabama on the other hand, uses left atrial pressure to determine the volume of fluid to infuse. The infusion rate is modulated by blood pressure parameters and periodic (1 hour) weighing of urine output. Although some success has been noted with this procedure, this method also necessitates invasive monitoring and is subject to the effects of other heart functions such as cardiac output, stroke work index, etc.

OBJECTS AND SUMMARY OF INVENTION

It is therefore an object of the present invention to provide an automated system which relies on urine output as the primary clinical parameter for fluid infusion, administration of medication and diagnostic substances and similar medical applications.

It is also an object of this invention to provide a method and apparatus which will accurately measure real time urine flow in catheterized patients.

It is a further object of the present invention to provide a method and apparatus useful as part of an automatic fluid resuscitation therapy for burn and trauma patients.

A still further object of this invention includes the development of apparatus useful in monitoring concentration of constituents of urine which may be useful in providing automatic adjustment to infusion programs for medication, fluids and diagnostic substances.

Another object of this invention is to provide such a system which compensates for variation in drop volume caused by changes in urine flow rate.

These and other objects are realized in a closed-loop system for controlled infusion of fluids, medication and diagnostic substances based on real time measurement of urine output of a patient. This closed system includes a urine drop counter including a drop chamber, means for successfully sensing occurrences of drops of urine within said drop chamber, an inlet means having an opening size and configuration adapted to form drops of substantially uniform volume, compensating means to adjust for changes in drop volume due to flow rate variation, and an outlet means for conduction urine from the chamber to a collection site. This urine drop counter receives urine flow from a small diameter tube connected at one end thereof to the inlet of the urine drop counter and at the other end to a bladder catheter associated with the patient. Signal processing means are coupled to the drop sensing means to provide monitoring of real time volumetric flow rate of the urine based on frequency of the drop occurrence as measured by the urine drop counter. This real time flow rate is compared to a predetermined flow rate selected for the specific patient. Any variance detected between the real time and predetermined flow rates is detected by comparator means and registered as an error signal output. The closed-loop system also includes a regulated infusion means adapted for automatically introducing such fluids, medications, or diagnostic substances to the patient at variable infusion rate based on the error signal output provided by the comparator. A computer means processes this error signal output and develops a correction signal to the regulated infusion means to change the infusion rate and thereby correct the patient fluid levels or concentrations of medication or diagnostic substances until a null reading is obtained at the comparator.

This invention includes the use of a self-compensating optical drop count apparatus for measuring volumetric fluid flow within the drop chamber. This aspect of the invention involves a light emitter and light detector which define a transmission path which is interrupted by each drop of urine falling through the drop chamber. Counting and timing circuitry are designed so that each drop is counted only once. The count is accumulated in a holding register where it may interface with external instrumentation equipment adapted to display the count and/or convert it to a volumetric measurement by multiplying it by the average volume of fluid contained in each drop. A compensation technique is utilized to maintain the intensity of the light beam generated by the light emitter as seen by the light detector at a constant level. Compensation is achieved in a closed-loop system which varies the drive current to the light emitter to compensate for long term variations that occur in the intensity of the light beam as sensed at the detector. Such long term variations could be caused by condensation or splashing of the fluid within the drop chamber or by the accumulation of dirt and dust on the chamber walls. This self compensating optical drop count apparatus avoids disruption of the measurement due to such variations.

These aspects of the invention are combined in a general method for closed-loop regulation of infusion based on real time measurement of urine production and composition which includes the steps of attaching one end of a small diameter, fluid filled tube to a patient's bladder catheter and the other end to a self compensating optical drop count apparatus as described to develop uniform urine flow in accordance with urine production and to develop a signal representing real time urine flow rate;

comparing said signal with a predetermined flow rate to develop an error signal corresponding to any variance between real time flow rate and said predetermined flow rate;

processing said error signal through a computer means having a control algorithm to develop a compensating signal and applying this signal to the regulated infusion means to adjust infusion flow rate appropriately. These steps are repeated in continuous order to maintain constant regulation of the infusion rate based on the real time urine output of the patient.

Other objects and features of the present invention will be apparent to one skilled in the art in view of the following detailed description in combination with the drawings in which:

FIG. 1 is a block diagram outlining the functional aspects of the invention; and FIG. 2 represents a block diagram of the drop counting system for measuring urine output.

DETAILED DESCRIPTION OF THE INVENTION

The present invention utilizes the real time measurement of urine output as the determinative factor in regulating infusion of fluids, medications and diagnostic substances in a closed-loop system. The use of real time measurements as opposed to prior art cumulative measurements of urine represents a significant advance over the prior art. Whereas, volumetric and weight measurements of urine output relate total urine production versus lapsed time, the present real time method permits instantaneous determination of flow rate and urine production. In other words, instead of having a nurse weigh or visually determine the volume of urine in a collection bag (i.e. 30 cc accumulated in one hour), the nurse could obtain a printout of flow rates calculated instantaneously with each successive drop or, more preferably, at regular intervals during the test period. The value of real time measurement over cumulative measurements is illustrated by the fact that a cumulative measurement of 30 cc per hour may have been realized through actual real time flow rates which may vary from one cc per hour to 60 cc per hour such that the average total accumulation is 30 cc. It is apparent that real time flow rate is the more valuable index of the physiological condition and changes within a patient.

Figure 1:
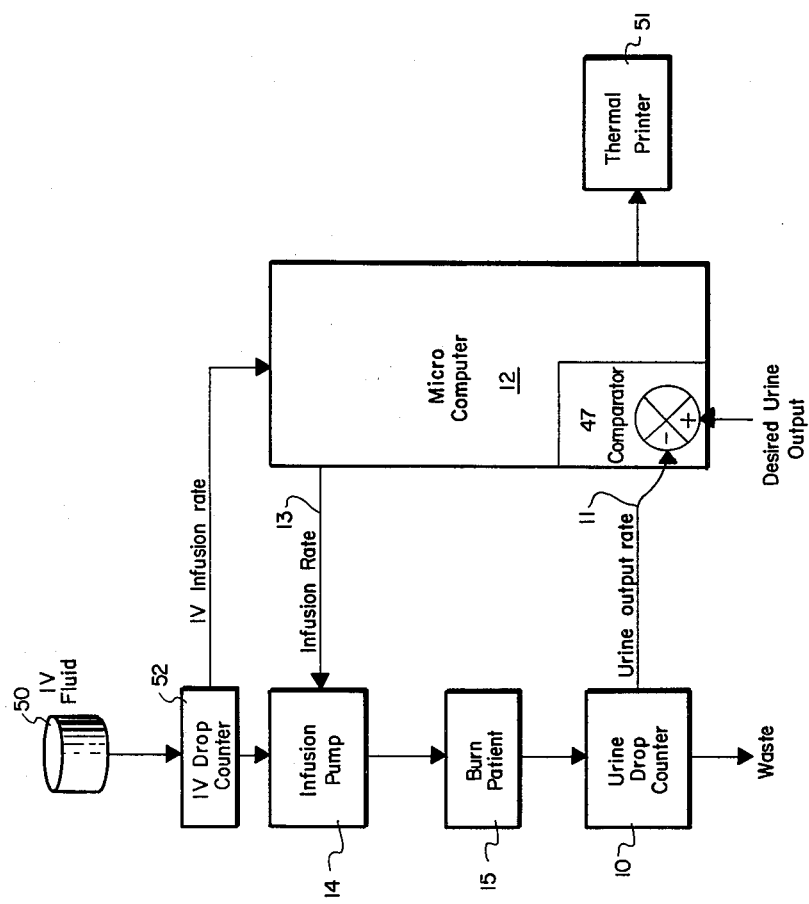

In the present invention, real time measurement of urine output is accomplished in a preferred system illustrated in FIG. 1. Real time measurements of urine flow are accomplished by means of a urine drop counter 10 which provides urine output 11 to a microprocessor controller or microcomputer means 12. This, in turn, calculates an adjusted infusion rate 13 which is used to stabilize an infusion pump 14 to an appropriate rate to bring a burn patient 15 to an improved fluid, medication or diagnostic substance level. This closed-loop represented by elements 10–15 is fully automated so that minimal attention is required by an attendant in maintaining the infusion rate adjustments to bring the patient to a stable level and maintain such level during the course of therapy.

An important element of this invention is the urine drop counter 10 which accomplishes the sequential detection of drops of urine produced by the patient. This apparatus is described in great detail in a U.S. Patent Application filed concurrently herewith under the title "Self Compensating Optical Drop Count Apparatus" which has a filing date of Oct. 9, 1979 and Ser. No. of 083,002. Although this device is fully explained in the referenced patent application, a basic illustration and discussion have been included herein for general information.

Figure 2:
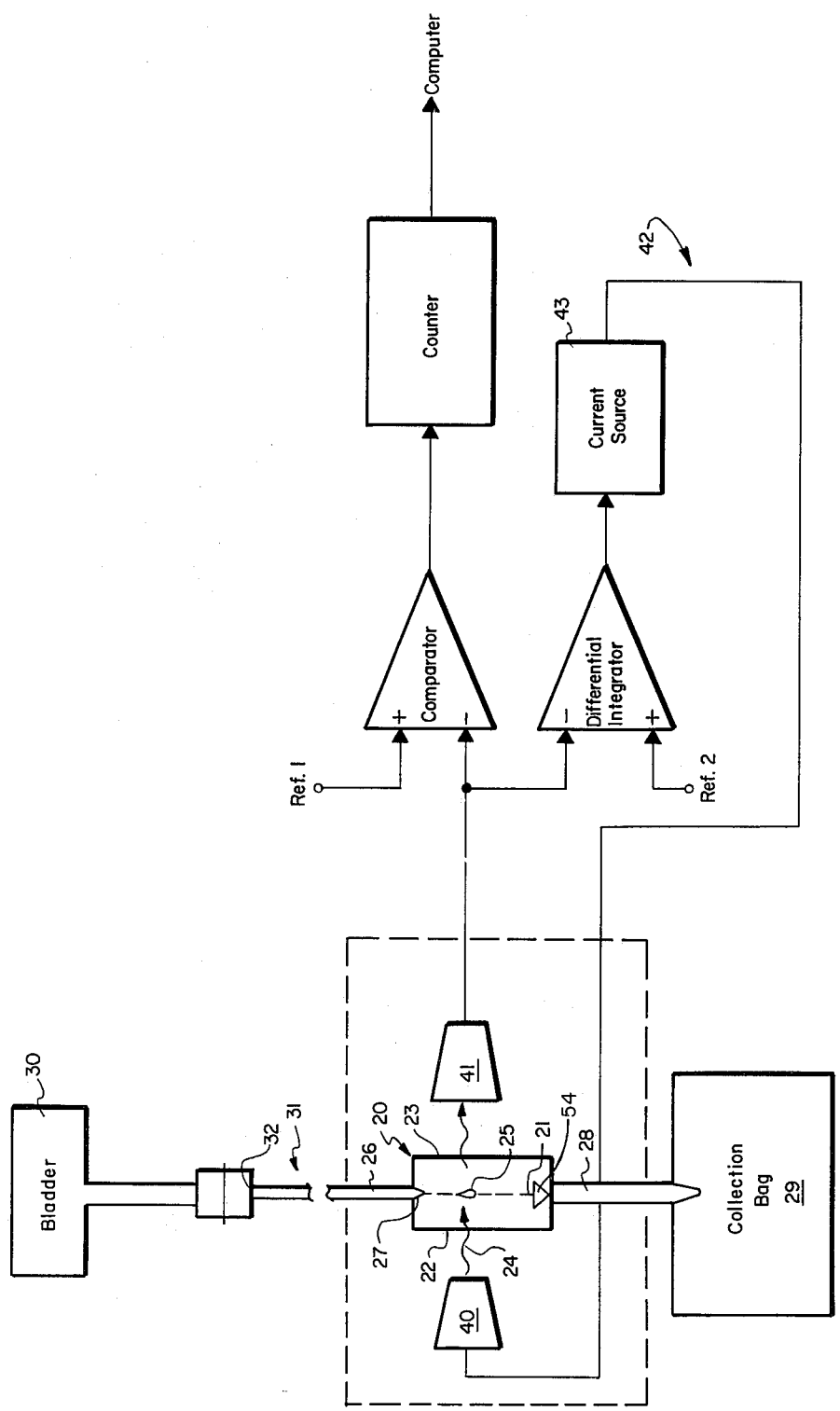

As shown in FIG. 2, the urine drop counter 10 includes a drop chamber 20 which houses a fluid drop path 21 and prevents interference from exterior influences such as wind, moisture, dust, etc. At least two opposing walls 22 and 23 permit transmission of selected radiation 24 as a means of detecting the occurrence of each drop of urine 25.

The drops of urine are formed at an inlet means 26 whose opening 27 is designed in size and configuration to form drops of substantially uniform volume for any given flow rate. Variations in drop size due to changing flow rates are compensated by the computer means discussed hereinafter. The opening of the inlet means projects within the chamber 20 and is thereby protected from exterior influence. Also coupled to the chamber is an outlet means 28 which provides a fluid path for the urine to a collection site 29.

In accordance with the present invention, urine measurements are to be made as urine is produced by the patient. It is therefore important that urine flow from the bladder 30 be consistent with the rate of production by the renal system. Accumulation of urine within the bladder would tend to distort the production rate since the urine drop counter would tend to show decrease in flow rate, with a subsequent surge upon urine discharge as the bladder is voided. Therefore, the present invention involves the use of a small diameter tube 31 which is connected at one end to the inlet means and is adapted at the other end for connection to a bladder catheter such as illustrated in FIG. 2. As used herein, "small diameter" means an inner tube diameter which is sufficiently small so that the flow rate therethrough does not exceed the rate of urine production by the patient's renal system. A conventional ½ inch i.d. tube for example, will tend to pass urine in surges. The smaller sized tube sets up a natural siphon effect which maintains a flow rate responsive to urine production.

To properly connect the tube to the drop counter and bladder catheter, it should be first filled with fluid so that a siphon effect is developed to maintain the urine flow in a continuous manner. In maintaining this uniform urine flow, it is not essential that the bladder be completely void. A residual urine content is permissable, provided that the residual volume remains relatively constant.

Because of the limited rate of urine production by the renal system, urine flow will be in droplets at the inlet means of the urine drop counter 27. The urine drop path 21 is oriented to intercept a radiation transmission path developed between an emitter 40 and a detector 41. As indicated in the referenced co-pending patent application, this emitter/detector combination can be an infrared system whose transmission is interrupted by each drop of urine to cause a pulse signal to be generated.

The emitter/detector combination therefore operates as means for successfully sensing occurrences of drops of urine within the chamber. To prevent false pulses, each main pulse triggers a timing circuit which blocks signals which might be caused from secondary droplets or inadvertent beam interruptions. An additional important feature of the urine drop counter is its ability to compensate for chamber clouding, condensation and other long term transmission interference material. As indicated in FIG. 2, this is accomplished by the use of a negative feedback circuit 42 which operates to increase the intensity of the emitter 40 to maintain the detector 41 at a quiescent point. This is achieved with the comparator circuit shown in FIG. 2 which drives the current source 43 to a sufficient level necessary to maintain the quiescent point for the detector 41. The practical consequence of this circuit is to enable accurate drop count measurement of urine without fear of false pulse measurement or inadvertent repetitive counting of urine droplets.

With an accurate flow rate established, a comparison is made with a predetermined urine flow rate which is programmed into the microcomputer 12. This desired urine output is specifically set by the physician or operator.

If a difference occurs between the predetermined urine output and that actually measured by the urine drop counter, an error signal is developed by comparator means 47. This error signal corresponds to the variance detected between the real time and predetermined flow rates and is processed by the microcomputer to effect a change in infusion rate 13.

If, for example, the urine output was measured to be at a rate lower than the desired urine output rate, the error signal generated by the comparator means would be processed by the microcomputer to increase the infusion rate 13 in accordance with an algorithm which would control the rate of increase to effect a null reading at the comparator means. Although this comparator means 47 is shown as a separate element, it should be understood that the microcomputer may provide the functions of a typical comparator circuit as opposed to having the comparator as a separate element.

To complete the closed-loop system, a regulated infusion means is provided for automatically introducing fluids, medications or diagnostic substances within the patient at a variable infusion rate, based on pre-set values and/or correction signals received from the computer means to adjust the infusion rate 13. Although numerous types of regulated infusion means can be developed, FIG. 1 illustrates a familiar intravenous fluid source 50 having Ringer's lactate solution or any other suitable sterile medium, which feeds into an infusion pump 14 which controls the actual rate of flow forced through the IV catheter. The infusion pump used in connection with the subject invention as an EXTRA-CORPOREAL Model 2100 which included a bubble detector, error-empty bottle detector and other alarm functions useful in the present system. Interface between the infusion pump and the microcomputer was a four bit parallel with individual digits transferred sequentially in a BCD format.

In addition to the closed-loop system, a printer 51 or other form of recording device can be coupled to the microcomputer to provide a written record of significant points of treatment, vital signs of patient, system alarms, time lapse indicators, etc.

This system has been tested extensively with dogs to determine the accuracy of urine measurement by the urine drop counter as opposed to the actual urine collected by volume. The actual results of such tests are summarized in the following table:

| Test | Duration (Hrs:Min) | % Burn | Weight (KG) | Vol (ml) Measured | Vol (ml) Accum. | % Error |
|---|---|---|---|---|---|---|
| URINE MEASUREMENT SYSTEM PERFORMANCE DATA (Dog Tests) | | | | | | |
| 4 | 13:45 | 0 | 25 | 840 | 828 | +1 |
| 5 | 8:00 | 0 | 26 | 364 | 355 | +3 |
| 6 | 8:30 | 0 | 23 | 192 | 189 | +2 |
| 7 | 8:00 | 0 | 25 | 419 | 412 | +2 |
| 9 | 3:00 | 30 | 26 | 58 | 56 | +3 |
| 10 | 3:20 | 30 | 23 | 33 | 31 | +6 |
| 12 | 8:40 | 35 | 24 | 236 | 228 | +3 |
| 13 | 8:00 | 40 | 24 | 84 | 80 | +5 |
| 14 | 10:00 | 40 | 27 | 157 | 149 | +5 |

As can be noted from % Error tabulation for the above indicated test, the present invention represents an accurate measurement technique.

As a safety check to verify actual output of the infusion flow pump, an additional drop counter 52 was placed in line with the infusion pump to monitor rate and cumulative IV solution administered. Output from this second drop counter 52 is directed to the microcomputer means to provide a means to monitor the need for IV bottle changes or to detect errors in infusion pump operation.

The system may also be modified with failure alarms such as flow sensor cable disconnect or other mechanical or electrical failures in the system. Input from the air embollism detector of the infusion pump can also be coupled to the computer to provide coordinated monitoring and recording on the printer of system failures along with a time log. It would be apparent to one skilled in the art that other modifications could be made to the overall system to provide additional sensors and input for blood pressure, environment conditions, and status reports on patient changes.

It will also be apparent to one skilled in the art that the subject closed-loop system is adaptable fo numerous treatment procedures. As previously indicated, burn and trauma patients experience extreme fluid level changes because of hemorrhage or exposed tissue and fluid loss thereby. The present system can be utilized to monitor fluid level by real time measurement of urine production and thereby stabilize the patient within safe limits.

As an illustrative example, a burn patient would be brought to a facility having the closed-loop system described herein and would be catheterized according to conventional clinical procedures. Such patients are usually brought to the facility with an IV bottle of Ringer's lactate solution attached and partially administered. The present system would be applied by fixing an IV drop counter 52 in lin with the IV solution and an infusion pump 14 which may be initially preset to maintain an infusion rate as calculated by the computer based on patient parameters or as estimated by the attending physician. This infusion rate is later modified as compensating signals are developed based on actual urine output.

The patient would then be coupled to the system by attaching a fluid filled siphon tube to the patient's bladder catheter on one end and at the other end to an optical drop count apparatus such as the urine drop counter 10 shown herein. The siphon tube is prefilled with sterile fluid to insure that siphon forces will maintain uniform flow from the patient's bladder to the urine drop counter. As urine drops fall into the drop chamber, they interrupt an infra-red emitter/detector radiation path and cause a pulse to be generated by circuitry attached to the drop counter. By using a self compensating negative feedback circuit as outlined herein effects of condensation or splashed droplets which cause long term partial interruption to the radiation transmission are avoided. As indicated earlier, this is because the referenced negative feedback circuitry is designed to increase emitter strength to maintain the detector at a quiescent point which enables the system to count only short term interruptions of the transmission.

In addition, a time lapse circuit is triggered with each droplet front to signal a blocking circuit which precludes counting any secondary droplets which might accompany the primary droplet. This time lapse circuit and associated negative feedback stabilizing circuit greatly improve the accuracy of urine flow rate which enables the system to provide a real time urine flow output measurement.

To further improved system accuracy compensation must be made for changes in the volume of each drop as flow rates change during therapy. Specifically, as urine flow increases, the drop size or volume increases also. The present system provides a control algorithm which automatically adjusts droplet volume in accordance with the real time rate of urine flow.

This real time urine output flow rate is then compared with a predetermined flow rate which is preset by an attending physician or may be calculated by the microcomputer based on specific patient parameters. The attached microcomputer may be used to ascertain this information by inquiry directed to the attendant. This is accomplished sequentially by asking for patient input as to weight, percent burn, time lapse from injury occurrence, total fluid previously administered, etc. Also, in addition to self checking circuitry, the computer can be used to direct the attendant to make certain safety checks of tube couplings, power connections and other mechanical connections within the system.

Once the system has been fully checked and is ready for operation, the system can be fully activated. The error signal developed by the comparator means is processed through the computer to develop a compensating signal in accordance with a PID control algorithm which is used to correct the infusion rate of IV solution to increase or decrease body fluid level. Control of the process by the PID appropriate algorithm is necessay to insure that maximum fluid control is maintained in accordance with a fluid flow rate which is acceptable to the body system. Variations in the PID algorithm may be appropriate for patients having differing forms of trauma or burn coverage. The computer means, of course, can select an appropriate fluid regime based on input from the attendant.

The compensating signal which is generated by the computer means triggers whatever change in infusion rate may be necessary to adjust the infusion pump to a proper level. The actual rate of infusion by the pump is continuously monitored by input to the microcomputer along with input from the IV drop counter. This data may be periodically read out at the printer 51 at predetermined time intervals to give a written comparison to the attendant of urine flow rate versus infusion rate, as well as other body parameters and total time lapse since start of therapy. With use of the subject closed-loop method of fluid infusion regulation, the patient can be maintained at a steady urine flow rate that would hopefully be indicative of a proper body fluid level.

In addition to control of fluid administration, this system may be used to monitor medication levels or levels of diagnostic material within the circulatory system. In fact, virtually any pharmaceutical agent or substance which has a defined renal clearance could be monitored by an appropriate sensitive electrode 54 (FIG. 2) positioned within the urine flow line. By constant monitoring of the substance concentration in the urine, the computer means could calculate plasma concentration based on the known clearance for the particular substance.

As an example, a physician may wish to maintain a certain level of penicillin within a patient due to infection. Knowing the clearance for penicillin, a sensor probe could be positioned in the vicinity of the urine drop count to sequentially check the concentration of pencillin in each drop of urine that passes. This could be converted by the microcomputer to actual plasma concentration and compared with a predetermined plasma concentration preset by the physician. If the plasma concentration is below the desired level, the computer could direct a correction signal to a reservoir of penicillin solution for introducton at a controlled rate into the IV. Such a feedback loop could be used to adjust the patient pencillin concentration to the appropriate level and maintain such a level throughout the therapy period.

Similarly, the subject closed-loop system can be used to monitor the occurrence of diagnostic agents as well as substances developed by the body which can be used in diagnostic determinations. For example, creatinine is a substance produced naturally by the body as a by-product of metabollism. Its construction in urine reaches a relatively stable value when the body metabolism is likewise stable. Any sudden shift in concentration of creatinine in the urine would therefore be an indication of possible renal failure or other physiological problems which may need immediate attention. A sensor for creatinine could be positioned in the vicinity of the urine drop count chamber or in the urine line to constantly monitor creatinine concentration. The computer can provide the appropriate alarm or administer preset therapy by modifcation of infusion rates or other medications in response to a correction signal to the infusion pump.

It will be apparent to those skilled in the art that numerous parameters can be monitored by the subject real time measurement system to take maximum advantage of urine production and composition as a diagnostic tool. These uses range from variations in rate of urine production to variations in composition within the urine, all of which can be subject to detection and measurement by the drop count method disclosed herein or by sensors 54 which are positioned within the urine flow line to detect concentration of urine constituents. It is therefore to be understood that the description provided herein is by way of exmple and is not to be construed as a limitation on the invention which is defined by the following claims.

We claim:

1. A closed loop system for controlled infusion of fluids, medication and diagnostic substances based on real time measurement of urine output of a patient, comprising:
   (a) a urine drop counter including
      (i) a drop chamber,
      (ii) means for successively sensing occurrences of drops of urine within said drop chamber,
      (iii) inlet means having an opening size and configuration adapted to form drops of substantially uniform volume,
      (iv) means to compensate for drop volume variation with variation in urine flow rate; and
      (v) outlet means adapted for conducting urine from said chamber to a collection site;
   (b) a small diameter tube connected at one end to said inlet means and adapted in length and configuration for connection at the other end to a bladder catheter to be associated with the patient, the catheter/tube combination including means to prevent rate of urine flow within said tube from exceeding rate of urine production by a patient's renal system;
   (c) comparator means coupled to said drop sensing means to provide monitoring of real time flow rate of said urine based on frequency of drop occurrence and to compare said real time flow rate with a predetermined flow rate selected for the patient, said comparator means including means to provide an error signal output corresponding to a variance detected between the real time and predetermined flow rates;
   (d) regulated infusion means adapted for automatically introducing said fluids, medications and diagnostic substances within said patient at variable infusion rates; and
   (e) computer means coupled to (i) the error signal output of the comparator means and (ii) the regulated infusion means, for processing said error signal and for providing an appropriate correction signal to said infusion means for adjusting infusion rates to thereby increase or decrease patient fluid levels or concentrations of medication or diagnostic substances until a null reading is obtained at the comparator based on changes in urine output.

2. An infusion system as defined in claim 1, wherein said urine drop counter comprises a radiation emitter and detector disposed on opposing sides of the drop chamber having radiation transmissive properties, said emitter and detector defining an optical path which intercepts a urine drop path within said chamber and operates to register a pulse signal upon interception of said radiation transmission by a drop of urine.

3. An infusion system as defined in claim 2, wherein the drop counter further comprises a negative feedback circuit which includes means to stabilize the detector at a quiescent point.

4. An infusion system as defined in claim 1, wherein said tube has an inner diameter of no more than approximately $\frac{1}{8}$ inch to enhance siphoning forces from the bladder catheter to the drop counter inlet means.

5. An infusion system as defined in claim 1, further including means wherein said initial infusion flow rate is automatically computed by said computer means based on input of patient parameters including weight, percent burn area, time lapse from occurrence of injury and amount of fluid previously administered.

6. An infusion system as defined in claim 1, further comprising specific chemical detecting means to be disposed within the urine drop counter 10 prior to the collection site to thereby adapt the system for real time detection of medication and diagnostic substance concentrations in combination with urine real time flow rates.

7. An infusion system as defined in claim 6, wherein said comparator further comprises means for setting a predetermined concentration level for said medication or diagnostic substances.

8. An infusion system as defined in claim 7, wherein said regulated infusion means includes means for attachment of a reservoir of medication or diagnostic substance whose rate of infusion is regulated by an error signal output from said comparator in response to a detected variance between said predetermined concentration and a real time concentration in the urine as detected by said chemical detector.

9. An infusion system as defined in claim 6, wherein said chemical detecting means is sensitive to medications and diagnostic substances selected from a group of substances having well defined renal clearances to permit close approximation of substance concentration within the patient based on relative substance concentration in the urine.

10. An infusion system as defined in claim 6, wherein said chemical detecting means is sensitive to variations in concentrations of criatinine.

11. An infusion system as defined in claim 6, wherein said chemical detecting means is sensitive to variations in concentrations of penicillin.

12. An infusion system as defined in claim 1, further comprising a second drop counter system coupled in line with said infusion means, said drop counter system including means to monitor flow rate and to provide input to said computer means for tabulating clinical data regarding infusion rate over a test period.

13. An infusion system as defined in claim 1, further comprising detection means in line with said regulated infusion means for signaling an alarm upon occurrence of an air embolism therein.

14. An infusion system as defined in claim 1, further comprising a printer coupled to said computer means, the combination computer means/printer including means to provide a printed history of treatment procedures, interruptions, infusion and urine flow data, time log and vital signs of the patient.

15. A method for closed loop regulation of infusion based on real time measurement of urine production and composition comprising the steps of:
(a) attaching one end of a fluid filled tube to a patient's bladder catheter and the other end to a self compensating, optical drop count apparatus to thereby maintain siphon forces useful to develop uniform urine flow therein in accordance with urine production and to develop a signal representing real time urine flow rate;
(b) comparing said signal with a predetermined flow rate to develop an error signal corresponding to any variance between real time flow rate and said predetermined flow rate;
(c) processing said error signal through a computer means having a control algorithm to develop a compensating signal;
(d) applying said compensating signal to a regulated infusion means coupled to said patient to adjust infusion flow rate to correct error signal; and
(e) repeating the previous steps to maintain a continuous closed loop control for adjusting infusion rates in response to real time need for increase and decrease in fluid, medication or diagnostic substance levels within the patient.

16. A method as defined in claim 15, wherein said method includes the more specific step of applying said compensating signal to an IV system with associated infusion pump to regulate rate of fluid flow to the patient.

17. A method as defined in claim 16, further comprising the step of attaching a self compensating optical fluid flow sensor to the infusion regulating means to provide real time infusion flow rate signals to the computer means.

18. A method as defined in claim 15, wherein the method includes the more specific step of attaching the fluid filled tube to a patient suffering from burn and trauma injury as part of a fluid resusitation treatment for automatically adjusting fluid infusion rates to correct fluid level excess or depletion as registered by changes in urine production.

19. A method as defined in claim 15, wherein said steps are repeated as part of a medication administration treatment wherein medication/plasma concentration is maintained at a predetermined level by monitoring medication concentration in urine production and adjusting medication infusion rates based on a known renal clearance factor for said medication.

20. A method as defined in claim 15, wherein said steps are repeated as part of a diagnostic procedure, said method including the specific step of detecting an abnormal rate of urine production as indication of renal failure.

21. A method as defined in claim 15, further comprising the step of detecting occurrence of creatinine within urine flow and signaling an alarm to alert attendants of possible renal failure.

22. A method as defined in claim 15, further comprising the step of processing said urine flow rate signal with means in concert with said computer means to compensate for changes in droplet volume consonant with changes in flow rate of said urine.

* * * * *